(12) United States Patent
Tanaka et al.

(10) Patent No.: US 7,729,868 B2
(45) Date of Patent: Jun. 1, 2010

(54) METHOD FOR ANALYZING STRUCTURE OF GLYCOPROTEIN

(75) Inventors: Koichi Tanaka, Kyoto (JP); Yoshinao Wada, Minoo (JP); Yuzo Yamazaki, Kyoto (JP); Yuko Fukuyama, Kyoto (JP)

(73) Assignees: Shimadzu Corporation, Kyoto (JP); Osaka Prefectural Hospital Organization, Osaka (JP)

( * ) Notice: Subject to any disclaimer, the term of this patent is extended or adjusted under 35 U.S.C. 154(b) by 891 days.

(21) Appl. No.: 11/104,543

(22) Filed: Apr. 13, 2005

(65) Prior Publication Data

US 2005/0234651 A1    Oct. 20, 2005

(30) Foreign Application Priority Data

Apr. 14, 2004 (JP) .............................. 2004-119336

(51) Int. Cl.
*G06F 19/00* (2006.01)
*C07K 1/14* (2006.01)
*H01J 49/26* (2006.01)

(52) U.S. Cl. ..................... 702/27; 530/395; 530/412; 250/282

(58) Field of Classification Search ................ None
See application file for complete search history.

(56) References Cited

OTHER PUBLICATIONS

Goodlett et al. Proteomics without polyacrylamide: qualitative and quantitative used of tandem mass spectrometry in proteome analysis. Functional and Integrative Genomics vol. 2, pp. 138-153 (2002).*

Ethier et al. Application of the StrOligo algorithm for the automated structure assignment of complex N-linked glycans from glycoproteins using tandem mass spectrometry. Rapid Communications in Mass Spectrometry vol. 17, pp. 2713-2720 (2003).*

Harvey Matrix-assisted laser desorption/ionization mass spectrometry of carbohydrates. Mass Spectrometry Reviews vol. 18, pp. 349-450 (1999).*

Ritchie et al. Precursor Ion Scanning for Detection and Structural Characterization of Heterogeneous Glycopeptide Mixtures Journal of the American Society for Mass Spectrometry vol. 13, pp. 1065-1077 (2002).*

Suzuki et al., "Shitsuryo Bunseki ni yoru Glycoproteomics II, MALDI-QIT Shitsuryo Bunseki Hou ni yoru Tou Peptide no Kouzou Kaiseki" ("Mass Spectrometric Glycoproteomics II, Structural Analysis of Glycopeptide Based on MALDI-QIT Mass Spectrometry"), Protein, Nucleic Acid and Enzyme, 2003, vol. 48, No. 8, pp. 1194-1199, Translation provided.

Yamagaki, Tohru et al., "Structural Analyses of Xyloglucan Heptasaccharide by the Post-source Decay Fragment Method Using Matrix-assisted Laser Desorption/Ionization Time-of-Flight Mass Spectrometry", Bioscience, Biotechnology, and Biochemistry, 1997, vol. 61, No. 8, pp. 1411-1414.

Notification of Reasons for Refusal for the Application No. 2004-119336 from Japan Patent Office mailed Sep. 15, 2009, Translation provided.

* cited by examiner

*Primary Examiner*—John S Brusca
(74) *Attorney, Agent, or Firm*—Cheng Law Group, PLLC

(57) ABSTRACT

The present invention provides a simplified method for analyzing a structure of glycoprotein capable of conducting a peptide sequence analysis, a sugar chain sequence analysis, and an analysis of a sugar chain binding site accurately and rapidly using a mass spectrometer.

6 Claims, 2 Drawing Sheets

SEQUENCE LISTING

<160> NUMBER OF SEQ ID NOS: 2

<210> SEQ ID NO 1
<211> LENGTH: 124
<212> TYPE: PRT
<213> ORGANISM: Bos taurus

<400> SEQUENCE: 1

Lys Glu Thr Ala Ala Ala Lys Phe Glu Arg Gln His Met Asp Ser Ser
 1               5                  10                  15

Thr Ser Ala Ala Ser Ser Ser Asn Tyr Cys Asn Gln Met Met Lys Ser
            20                  25                  30

Arg Asn Leu Thr Lys Asp Arg Cys Lys Pro Val Asn Thr Phe Val His
        35                  40                  45

```
Glu Ser Leu Ala Asp Val Gln Ala Val Cys Ser Gln Lys Asn Val Ala
     50                  55                  60

Cys Lys Asn Gly Gln Thr Asn Cys Tyr Gln Ser Tyr Ser Thr Met Ser
 65              70                  75                      80

Ile Thr Asp Cys Arg Glu Thr Gly Ser Ser Lys Tyr Pro Asn Cys Ala
                 85                  90                  95

Tyr Lys Thr Thr Gln Ala Asn Lys His Ile Ile Val Ala Cys Glu Gly
            100                 105                 110

Asn Pro Tyr Val Pro Val His Phe Asp Ala Ser Val
         115                 120

<210> SEQ ID NO 2
<211> LENGTH: 6
<212> TYPE: PRT
<213> ORGANISM: Bos taurus

<400> SEQUENCE: 2

Ser Arg Asn Leu Thr Lys
 1               5
```

METHOD FOR ANALYZING STRUCTURE OF GLYCOPROTEIN

BACKGROUND OF THE INVENTION

1. Field of the Invention

The present invention relates to a method for analyzing a structure of glycoprotein or glycopeptide using a mass spectrometer capable of executing a second or higher order MS analysis.

2. Disclosure of the Related Art

For analyzing a structure of a glycoprotein or a glycopeptide, it is necessary to acquire information about (i) peptide sequence, (ii) sugar chain sequence, and (iii) sugar chain binding site.

In a method for analyzing a glycoprotein or a glycopeptide, sugar chains are separated from the glycoprotein or the glycopeptide (hereinafter, simply referred to as "glycoprotein") in an enzymatic or chemical manner and then the resultant protein or peptide (hereinafter, simply referred to as "protein") and sugar chains are separately analyzed. For such analysis, a mass spectrometer is used in these days. In mass spectrometry, a post-source decay (PSD) function and a collision induced dissociation (CID) function are utilized. These functions will give important structure information for sugar chains and fragments of a peptide.

As a method for separately analyzing proteins and sugar chains, for example, the following manner is exemplified. First, a glycoprotein obtained by two dimensional electrophoresis or a variety of chromatography is fragmented into peptides or glycopeptides with a protease, and further separated into sugar chains and peptides by glycanase digestion or β-dissociation. Then the resultant peptides are chemically tagged at an amino acid residue to mark the binding site of sugar chain, and then sequencing analysis of peptides and identification of sugar chain binding site are conducted by a peptide mass finger printing (PMF) based on MS analysis or by an MS/MS analysis based on the CID and PSD functions with a mass spectrometer. On the other hand, as to the sugar chains, a sequencing analysis of sugar chains is conducted by MS and MS/MS analyses using a mass spectrometer, by a multi-dimensional mapping using a HPLC, or by a sequential digestion with glycosidase.

Also an attempt is made to directly analyze a structure of glycoprotein in its native form without separating sugar chains as above described. For achieving this, an $MS^n$ analysis by a mass spectrometer is utilized. A Fourier transformation ion cyclotron resonance mass spectrometer (FTICR-MS) is known as a mass spectrometer that enables mass spectrometric analysis of glycoprotein. In such a mass spectrometer, an electron capture dissociation (ECD) function and an infrared multiphoton dissociation (IRMPD) function that were recently developed are specifically used. The ECD function gives information about sugar chain binding site and molecular weight of sugar chain because it can cut only a peptide backbone without destroying sugar chains. The IRMPD function gives sequence information of sugar chain because it can cut only sugar chains without cutting a peptide backbone. Therefore, a peptide sequencing analysis, a sugar chain sequencing analysis, and an analysis of sugar chain binding site with a FTICR-MS is conducted by combining these two functions.

SUMMARY OF THE INVENTION

In the method in which sugar chains and proteins are separated and separately analyzed, not only a long time is required for overall analysis, but also a difficulty arises in discussing the meaning of sugar chain modification, namely, what kind of sugar chain binds to what position in what kind of protein and how to function, when considering the functionality of the glycoprotein.

Another problem lies in that in the post-source dissociation (PSD) and the collision induced dissociation (CID) functions of a mass spectrometer that is often used in such an analysis, since both sugar chains and peptide chains of protein are individually fragmented, the spectrum is complicated and difficult to be analyzed. According to these functions, since sugar chains are more likely to dissociate than peptide chains, it is difficult to obtain fragments in such a state that sugar chains are bound to peptide chains, and hence it is difficult to obtain information about sugar chain binding sites.

On the other hand, in the method of measuring a glycoprotein without separating sugar chains and proteins, a FTICR mass spectrometer is used as described above. However, this apparatus is expensive and bulky, and takes a lot of labor in maintenance and management. In fragmentation of a peptide chain part based on the ECD function used in the FTICR mass spectrometer, generated fragments are too poor to acquire peptide sequence information. Additionally, it is necessary to optimize a large number of parameters during the operation, so that the measurement is not easy. Further, when a structural analysis of glycoprotein is conducted using a single FTICR mass spectrometer combining the ECD function and the IRMPD function, for example, a filament for ECD must be detached when a device for the IRMPD function is attached, so that the ECD analysis can not be conducted under the setting for the IRMPD analysis. In brief, it takes a lot of time and labor to analyze a glycoprotein using both of the IRMPD function and the ECD function.

It is an object of the present invention to provide a simplified method for analyzing a structure of glycoprotein capable of conducting a peptide sequence analysis, a sugar chain sequence analysis, and analysis of a sugar chain binding site accurately and rapidly using a mass spectrometer.

Inventors of the present application found that the above object of the invention was achieved by using a mass spectrometer capable of conducting a second or higher order MS analysis, selecting protonated molecules and metal ion-adducted molecules in mass spectrum as precursors to conduct an $MS^n$ analysis for each of the precursor ions, and accomplished the present invention.

The present invention includes the following aspects.

(1) A method for analyzing a structure of glycoprotein or glycopeptide comprising the steps of:

conducting an MS analysis of a glycoprotein or a glycopeptide using a mass spectrometer capable of conducting a second or higher order MS analysis;

conducting an $MS^n$ analysis by selecting:

an A-adducted molecule represented by $[M+A]^+$ in which a positively charged ion $A^+$ that is likely to add to a protein or a peptide adds to a specific glycoprotein molecule or a specific glycopeptide molecule M measured in the MS analysis, and a B-adducted molecule represented by $[M+B]^+$ in which a positively charged ion $B^+$ that is likely to add to a sugar chain adds to the specific glycoprotein molecule or the specific glycopeptide molecule M, respectively as a precursor ion;

identifying a primary structure of a protein or a peptide and a sugar chain binding site from an A-adducted molecule in an $MS^n$ analysis data obtained by using the A-adducted molecule represented by $[M+A]^+$ as a precursor ion; and identifying a primary structure of a sugar chain from a B-adducted molecule in an $MS^n$ analysis data obtained by using the B-adducted molecule represented by $[M+B]^+$ as a precursor ion.

(2) The method for analyzing a structure of glycoprotein or glycopeptide according to the above (1), wherein the positively charged ion $A^+$ that is likely to add to a protein or a peptide is a proton.

(3) The method for analyzing a structure of glycoprotein or glycopeptide according to the above (1) or (2), wherein the positively charged ion $B^+$ that is likely to add to a sugar chain is a metal ion.

(4) The method for analyzing a structure of glycoprotein or glycopeptide according to the above (3), wherein the metal ion is a sodium ion.

(5) The method for analyzing a structure of glycoprotein or glycopeptide according to any one of the above (1) to (4), wherein the primary structure of protein or peptide, the primary structure of sugar chain, and the sugar chain binding site are identified using a mass spectrometer in which a single ion source is used.

(6) The method for analyzing a structure of glycoprotein or glycopeptide according to any one of the above (1) to (5), wherein the mass spectrometer is a MALDI-QIT-TOF (Matrix Assisted Laser Desorption/Ionization Quadrupole Ion Trap Time of Flight) mass spectrometer.

According to the present invention, it is possible to provide a simplified method for analyzing a structure of glycoprotein capable of conducting a peptide sequence analysis, a sugar chain sequence analysis, and analysis of a sugar chain binding site accurately and rapidly using a mass spectrometer.

BRIEF DESCRIPTION OF THE DRAWINGS

FIG. 1($b$) is an amino acid sequence of a peptide part of RNase B (SEQ ID NO. 1); and FIG. 1($c$) is a structure of glycopeptide corresponding to the precursor ion in FIG. 1($a$) and major fragmentations thereof (SEQ ID NO. 2)

DETAILED DESCRIPTION OF THE INVENTION

Figure 1:
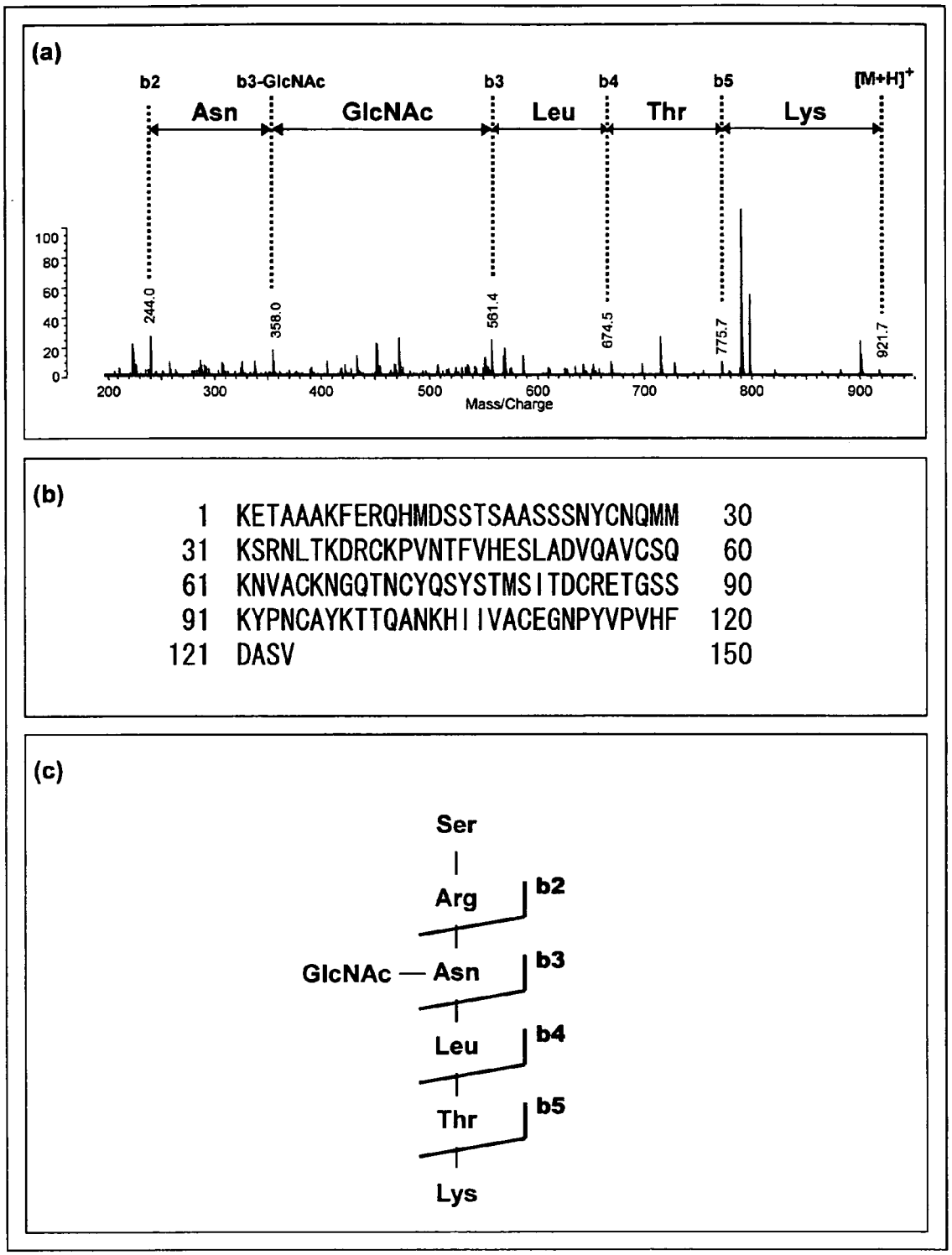
FIG. 1($a$) is an $MS^3$ spectrum of a glycopeptide of RNase B when a protonated molecule is used as a precursor ion.

In the present invention, MS and $MS^n$ analyses of a glycoprotein or glycopeptide sample are conducted using a mass spectrometer capable of executing a second or higher order MS analysis in mass spectrometric analysis (MS analysis). In the present specification, in analyses using a mass spectrometer, a first analysis of a sample is referred to as an MS analysis, and a second analysis (MS/MS analysis) conducted using a specific ion selected from ion peaks of a spectrum obtained in the MS analysis as a precursor ion is referred to as an $MS^2$ analysis. Likewise, an nth order MS analysis conducted using a specific ion peak selected from ion peaks of the spectrum obtained in the $MS^{n-1}$ analysis as a precursor ion is referred to as an $MS^n$ analysis, and called an nth order MS analysis.

A glycoprotein or glycopeptide may be chemically fragmented or enzymatically digested as is necessary. However, the procedure should be selected such that sugar chains and peptide chains in the sample will not break. The sample glycoprotein or glycopeptide may be fragmented into a plurality of smaller peptide molecules and glycopeptide molecules (namely, peptide molecules having sugar chains). These molecules may be analyzed by subjecting the mixed sample to an MS analysis. In the following, the method of the present invention will be explained for the case of analyzing the mixed sample as described above.

Through an MS analysis of the mixed sample, a plurality of peaks for peptides and glycopeptides are detected. Peptides may be identified by a conventional peptide sequencing. Glycopeptides may be identified in the following manner.

In a spectrum obtained in the MS analysis, an A-adducted molecule represented by $[M+A]^+$ in which a positively charged ion $A^+$ that is likely to add to a peptide adds to a specific glycopeptide molecule M, and a B-adducted molecule represented by $[M+B]^+$ in which a positively charged ion $B^+$ that is likely to add to a sugar chain adds to the specific glycopeptide molecule M are separately selected as precursor ions and respectively subjected to an $MS^2$ analysis.

As a positively charged ion $A^+$ likely to add to a peptide in inonization in a positive mode measurement of the MALDI method, a proton is exemplified. In other words, a peptide is detected more easily in the form that a proton is added thereto. On the other hand, as a positively charged ion $B^+$ likely to add to a sugar chain, a metal ion is exemplified. As the metal ion, a sodium ion is exemplified. In other words, a sugar chain is detected more easily in the form that a metal ion such as sodium ion is added thereto.

In the present specification, what a peptide is likely to add a proton means that a peptide is more likely to attract a proton than other positively charged ions. In this case, a protonated molecule represented by $[M+H]^+$ in which a proton adds to a specific glycopeptide molecule M is selected as a precursor ion.

Likewise, what a sugar is likely to add a metal means that a sugar is more likely to attract a metal ion than other positively charged ions. In this case, a metal ion-adducted molecular in which a metal ion adds to a specific glycopeptide molecule M is selected as a precursor ion. When the metal ion is a sodium ion, a sodium ion-adducted molecule represented by $[M+Na]^+$ in which a sodium ion $Na^+$ adds to the specific one glycopeptide molecule M is selected as a precursor ion.

In an $MS^2$ analysis using $[M+A]^+$ as a precursor ion, a plurality of fragments sequentially losing amino acids in the peptide chain one by one are mainly obtained. This allows acquisition of peptide sequence information and identification of a sugar chain binding site.

In an $MS^2$ analysis using $[M+B]^+$ as a precursor ion, a plurality of fragments that are made up of only sugar chains are mainly obtained. This allows acquisition of sequence information of the sugar chains.

In both $MS^2$ analyses, an $MS^n$ analysis may be conducted by selecting a precursor ion from the obtained fragments to acquire more specific sequence information about the peptide or sugar chains. Since the fragments obtained in each $MS^n$ analysis can be assigned to a specific one precursor, it is possible to accurately execute a structural analysis regarding a target molecular ion.

EXAMPLES

In the following, the method of the present invention will be explained in more detail for the case where glycoprotein ribonuclease B (RNase B) is used as a sample. It should be noted that the present invention is not limited to these examples. RNase B is believed to have a single oligosaccharide chain bound to asparagine and consisting of two N-acetylglucosamine (GlcNAc) residues and 5-9 mannose residues.

162 µg of RNase B was reduced with 10 mg of dithiothreitol in 950 µL of 8M urea solution, and then digested with 3.24 µg of lysyl endopeptidase (protein:substrate=50:1 (wt/wt)). The resultant digest was analyzed by using a Matrix Assisted Laser Desorption/Ionization Quadrupole Ion Trap Time of Flight mass spectrometer (MALDI-QIT-TOF-MS) without conducting desalting and any other purification process.

As a matrix, a solution of 2,5-dihydroxybenzoic acid (DHB) dissolved in a 40:60 (v/v) mixture of acetonitrile and ultra pure water in concentration of 12.5 mg/mL was used. 0.2 µL aliquot of an enzymatic digest solution prepared in a concentration of 20 pmol/µL was mixed into 0.5 µL of matrix solution for measurement.

In the MS analysis of an enzymatic digest of RNase B, a plurality of peptides were obtained as protonated molecules at a coverage of about 77%. $MS^2$ analyses for these gave structural information about peptides as a great number of y-series and b-series fragments (m/z 2225.5, 2230.5, 2799.1, and 2877.1).

In the MS analysis of an enzymatic digest of RNase B, a plurality of glycopeptides gave five peaks (m/z 1935.9, 2098.0, 2260.2, 2422.3, and 2584.5) as protonated molecules. This shows that the oligosaccharide chain of the RNase B consists of two GlcNAc residues and 5-9 hexose residues. From these five glycopeptides, the protonated molecule at m/z 1935.9 having the highest intensity and the sodium ion-adducted molecule (m/z 1957.9) corresponding to the same glycopeptide were selected as precursor ions, and an $MS^n$ analysis was conducted for each of the precursor ions.

In an $MS^2$ analysis for the protonated molecule (m/z 1935.9), ions (m/z 801.7 and 921.7) corresponding to the peptides to which one GlcNAc is added are predominantly detected. The product ion corresponding to the peak at m/z 801.7 is generated by cleaving of the GlcNAc ring of the product ion corresponding to the peak at m/z 921.7. Further, an $MS^3$ analysis was conducted while selecting ion at m/z 921.7 as a precursor ion. The obtained spectrum is shown in FIG. 1(a). In FIG. 1(a), the horizontal axis represents Mass/Charge, and the vertical axis represents relative intensity of ion. The fragment ions arising from bond cleavages along the GlcNAc-bearing peptide backbone provide information about the sugar chain binding site as well as the peptide sequence. FIG. 1(b) shows an amino acid sequence of the peptide part of RNase B (SEQ ID:1 of the sequence listing), and FIG. 1(c) shows a structure of the glycopeptide (amino acid sequence of the peptide part: SEQ ID NO: 2 in the sequence listing) corresponding to the precursor ion in FIG. 1(a) and major fragmentations thereof.

Figure 2:
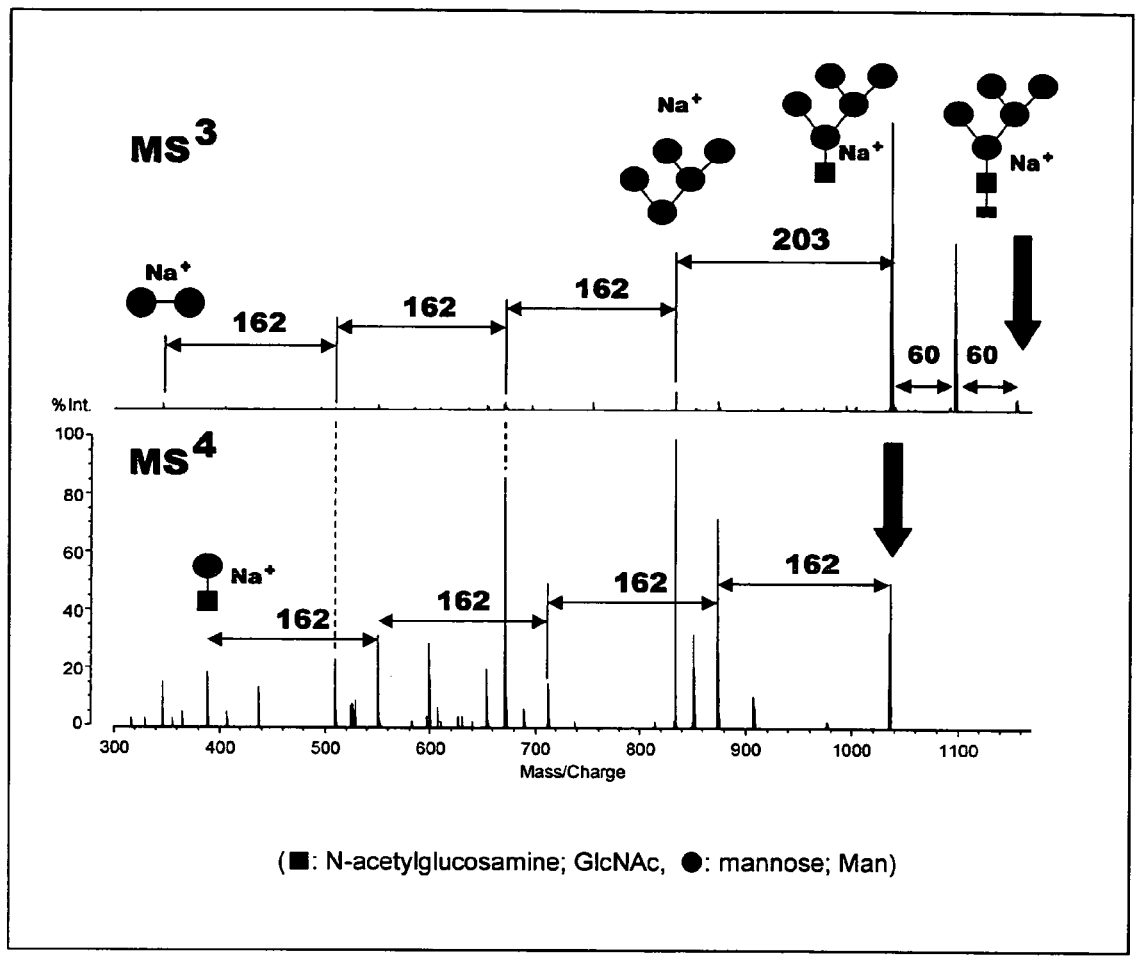
FIG. 2 shows $MS^3$ and $MS^4$ spectrums of a glycopeptide of RNase B when a sodium ion-adducted molecule is used as a precursor ion.

On the other hand, in an $MS^2$ analysis for the sodium ion-adducted molecule (m/z 1957.9), a plurality of peaks of sodium ion-adducted molecule mainly formed of sugar chains were detected. These peaks were further subjected to $MS^3$ and $MS^4$ analyses. The obtained spectrums are shown in FIG. 2. In FIG. 2, the horizontal axis represents Mass/Charge, and the vertical axis represents relative intensity of ion (% Int.). Sugar chain fragments detected as sodium ion-adducted molecules thus obtained gave sequence information of the sugar chain part of RNase B.

By conducting $MS^n$ analyses on protonated molecules and sodium ion-adducted molecules in addition to the MS analysis in the manner as described above, it becomes possible to determine a sugar chain sequence, a peptide sequence, and a sugar chain binding site of a glycoprotein with a single mass spectrometer using a single ion source.

In conclusion, the analytical method of glycoprotein according to the present invention provides the following effects.

1. In $MS^n$ analyses, a plurality of precursor ions that are selected for a specific molecule all originate from the same molecule. Therefore, every structural information that is obtained from these precursor ions can be directly assigned to that molecule. This enables accurate analysis.

2. In $MS^n$ analyses, analyses of a specific glycoprotein and a specific glycopeptide can be executed in the condition that sugar chains are added thereto. Therefore, from the obtained data, it is possible to discuss the function of a specific glycoprotein while considering about sugar chain modification, that is, what kind of sugar chain binds to what position in what kind of protein.

3. Since a structure analysis can be conducted using a glycopeptide or a glycoprotein prepared as a single sample with only a single mass spectrometer using a single ion source, it is possible to conduct rapid analysis. Further, since the basic setting does not need to be changed for each $MS^n$ analysis, the operation is simplified.

In the above Example, concrete form within the scope of the present invention is shown, however, the present invention may be practiced in various forms without limited to the above form. The above Example is given just for exemplification in all respects and should not be interpreted in a limitative manner. Any modifications made within the equivalents of claims fall in the scope of the present invention.

What is claimed is:

1. A method for analyzing a structure of glycoprotein or glycopeptide comprising the steps of:
   (A) conducting an MS analysis of a single sample of a glycoprotein or a glycopeptide using a mass spectrometer capable of conducting a second or higher order MS analysis to obtain
      (i) an A-adducted molecule represented by $[M+A]^+$ in which a positively charged ion $A^+$ that is likely to add to a protein or a peptide adds to a specific glycoprotein molecule or a specific glycopeptide molecule M and
      (ii) a B-adducted molecule represented by $[M+B]^+$ in which a positively charged ion $B^+$ that is likely to add to a sugar chain adds to the specific glycoprotein molecule or the specific glycopeptide molecule M;
   (B) conducting a second or higher order $MS^n$ analysis by selecting said A-adducted molecule represented by $[M+A]^+$ measured in said MS analysis as a precursor ion to obtain an A-adducted glycoprotein or glycopeptide and
   by selecting said B-adducted molecule represented by $[M+B]^+$ measured in said MS analysis as a precursor ion to obtain a B-adducted sugar chain;
   (C) identifying a primary structure of a protein or a peptide and a sugar chain binding site using said A-adducted glycoprotein or glycopeptide; and
   (D) identifying a primary structure of a sugar chain using said B-adducted sugar chain.

2. The method for analyzing a structure of glycoprotein or glycopeptide according to claim 1, wherein the positively charged ion $A^+$ that is likely to add to a protein or a peptide is a proton.

3. The method for analyzing a structure of glycoprotein or glycopeptide according to claim 1, wherein the positively charged ion $B^+$ that is likely to add to a sugar chain is a metal ion.

4. The method for analyzing a structure of glycoprotein or glycopeptide according to claim 3, wherein the metal ion is a sodium ion.

5. The method for analyzing a structure of glycoprotein or glycopeptide according to claim 1, wherein the primary structure of protein or peptide, the primary structure of sugar chain, and the sugar chain binding site are identified using a mass spectrometer in which a single ion source is used.

6. The method for analyzing a structure of glycoprotein or glycopeptide according to claim 1, wherein the mass spectrometer is a MALDI-QIT-TOF (Matrix Assisted Laser Desorption/Ionization Quadrupole Ion Trap Time of Flight) mass spectrometer.

* * * * *